US012758184B2

(12) United States Patent
Wekselman et al.

(10) Patent No.: US 12,758,184 B2
(45) Date of Patent: Oct. 13, 2026

(54) SYSTEM AND METHOD OF TISSUE CONTACT ASSESSMENT FOR BALLOON CATHETER ABLATION

(71) Applicant: BIOSENSE WEBSTER (ISRAEL) LTD., Yokneam (IL)

(72) Inventors: Guy Wekselman, Tel Aviv (IL); Dan Sztejnberg, Hertzilyz (IL); Yair Palti, Hertzilya (IL); David Haimovich, Haifa (IL); Lior Greenbaum, Zoran (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 293 days.

(21) Appl. No.: 17/368,144

(22) Filed: Jul. 6, 2021

(65) Prior Publication Data

US 2023/0008606 A1 Jan. 12, 2023

(51) Int. Cl.
*A61B 8/00* (2006.01)
*A61B 8/06* (2006.01)
(Continued)

(52) U.S. Cl.
CPC .............. *A61B 8/4245* (2013.01); *A61B 8/06* (2013.01); *A61B 8/12* (2013.01); *A61B 8/461* (2013.01);
(Continued)

(58) Field of Classification Search
CPC ........... A61B 8/4245; A61B 8/06; A61B 8/12; A61B 8/461; A61B 18/1206;
(Continued)

(56) References Cited

U.S. PATENT DOCUMENTS 5,078,714 A 1/1992 Katims
5,341,807 A 8/1994 Nardella
(Continued)

FOREIGN PATENT DOCUMENTS

CA 2285342 A1 10/1998
EP 1159036 B1 * 6/2007 ............ A61B 18/00
(Continued)

OTHER PUBLICATIONS

European Search report for corresponding EPA No. 22183017.7 dated Nov. 18, 2022.
(Continued)

*Primary Examiner* — Joel Lamprecht
*Assistant Examiner* — James F Mcdonald, III
(74) *Attorney, Agent, or Firm* — Clayton, McKay & Bailey, PC

(57) ABSTRACT

In one embodiment, a medical system includes a catheter configured to be inserted into a cavity of a body of a living subject, and including an inflatable balloon comprising electrodes, the inflatable balloon being configured to press the electrodes against tissue of the cavity and at least partially block blood flow in the cavity, an ultrasound probe configured to provide velocity measurements of the blood flow in the cavity over time, a processor configured to assess a quality of contact of the electrodes with the tissue responsively to at least one of the velocity measurements of the blood flow in the cavity, and output an indication of the quality of contact to an output device, and a power supply configured to provide at least one electrical signal to the electrodes in order to ablate the tissue of the cavity.

11 Claims, 8 Drawing Sheets

(51) Int. Cl.

| | |
|---|---|
| ***A61B 8/12*** | (2006.01) |
| ***A61B 18/12*** | (2006.01) |
| ***A61B 18/14*** | (2006.01) |
| *A61B 18/00* | (2006.01) |

(52) U.S. Cl.
CPC ...... *A61B 18/1206* (2013.01); *A61B 18/1492* (2013.01); *A61B 2018/0022* (2013.01); *A61B 2018/00351* (2013.01); *A61B 2018/00577* (2013.01); *A61B 2018/00994* (2013.01)

(58) Field of Classification Search
CPC ........ A61B 18/1492; A61B 2018/0022; A61B 2018/00351; A61B 2018/00577; A61B 2018/00994; A61B 8/0883; A61B 8/0891; A61B 8/4254; A61B 8/445; A61B 2018/00375; A61B 2018/00863; A61B 2090/065; A61B 2218/002; A61B 18/12; A61B 34/20; A61B 90/06; A61B 17/12; A61B 2018/00595; A61B 2018/1467; A61B 2034/2051; A61B 2034/2063; A61B 2034/2065
See application file for complete search history.

(56) References Cited

U.S. PATENT DOCUMENTS

| | | | | |
|---|---|---|---|---|
| 5,391,199 | A | 2/1995 | Ben | |
| 5,409,000 | A * | 4/1995 | Imran | A61B 8/12 600/374 |
| 5,447,529 | A | 9/1995 | Marchlinski | |
| 5,469,857 | A | 11/1995 | Laurent | |
| 5,662,108 | A | 9/1997 | Budd | |
| 5,673,704 | A | 10/1997 | Marchlinski | |
| 5,752,522 | A | 5/1998 | Murphy | |
| 5,836,874 | A | 11/1998 | Swanson | |
| 5,836,990 | A | 11/1998 | Li | |
| 5,891,095 | A | 4/1999 | Eggers | |
| 5,935,079 | A | 8/1999 | Swanson | |
| 6,239,724 | B1 | 5/2001 | Doron | |
| 6,266,551 | B1 | 7/2001 | Osadchy | |
| 6,332,089 | B1 | 12/2001 | Acker | |
| 6,484,118 | B1 | 11/2002 | Govari | |
| 6,618,612 | B1 | 9/2003 | Acker | |
| 6,690,963 | B2 | 2/2004 | Ben | |
| 6,716,166 | B2 | 4/2004 | Govari | |
| 6,773,402 | B2 | 8/2004 | Govari | |
| 7,756,576 | B2 | 7/2010 | Levin | |
| 7,848,787 | B2 | 12/2010 | Osadchy | |
| 7,869,865 | B2 | 1/2011 | Govari | |
| 10,918,310 | B2 | 2/2021 | Cohen | |
| 11,039,883 | B1 * | 6/2021 | Boveja | A61B 8/0883 |
| 2002/0065455 | A1 | 5/2002 | Ben | |
| 2002/0087156 | A1 * | 7/2002 | Maguire | A61B 18/1492 606/41 |
| 2003/0120150 | A1 | 6/2003 | Govari | |
| 2004/0068178 | A1 | 4/2004 | Govari | |
| 2006/0259023 | A1 | 11/2006 | Abboud | |
| 2007/0100332 | A1 | 5/2007 | Paul | |
| 2007/0167801 | A1 * | 7/2007 | Webler | G06T 19/00 600/459 |
| 2009/0093806 | A1 | 4/2009 | Govari | |
| 2009/0138007 | A1 | 5/2009 | Govari | |
| 2011/0082452 | A1 | 4/2011 | Melsky | |
| 2011/0152684 | A1 | 6/2011 | Altmann | |
| 2014/0005706 | A1 | 1/2014 | Gelfand et al. | |
| 2015/0099989 | A1 * | 4/2015 | Kobayashi | A61B 5/026 606/49 |
| 2015/0320472 | A1 * | 11/2015 | Ghaffari | A61B 18/24 606/21 |
| 2017/0143201 | A1 | 5/2017 | Claude | |
| 2017/0347896 | A1 | 12/2017 | Keyes | |
| 2019/0307331 | A1 * | 10/2019 | Saadat | A61B 34/20 |
| 2019/0343580 | A1 | 11/2019 | Nguyen | |
| 2020/0038638 | A1 | 2/2020 | Gliner | |
| 2021/0077180 | A1 | 3/2021 | Govari | |
| 2021/0169394 | A1 * | 6/2021 | Chou | A61B 34/10 |

FOREIGN PATENT DOCUMENTS

| | | | | |
|---|---|---|---|---|
| WO | WO1996005786 | A1 | 2/1996 | |
| WO | 2014189887 | A2 | 11/2014 | |
| WO | WO-2015200518 | A1 * | 12/2015 | A61B 18/1492 |
| WO | WO-2019042769 | A1 * | 3/2019 | A61B 18/1492 |
| WO | WO2021001338 | A1 | 1/2021 | |

OTHER PUBLICATIONS

Notification of Reasons for Refusal for JP Application No. 2022-108232 dated Mar. 17, 2026.

* cited by examiner

SYSTEM AND METHOD OF TISSUE CONTACT ASSESSMENT FOR BALLOON CATHETER ABLATION

FIELD OF THE INVENTION

The present invention relates to medical devices, and in particular, but not exclusively to, tissue contact assessment.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral artery, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied to the tip electrode(s) of the ablating catheter, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known that impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

SUMMARY

There is provided in accordance with an embodiment of the present invention, a medical system, including a catheter configured to be inserted into a cavity of a body of a living subject, and including an inflatable balloon including electrodes, the inflatable balloon being configured to press the electrodes against tissue of the cavity and at least partially block blood flow in the cavity, an ultrasound probe configured to provide velocity measurements of the blood flow in the cavity over time, a processor configured to assess a quality of contact of the electrodes with the tissue responsively to at least one of the velocity measurements of the blood flow in the cavity, and output an indication of the quality of contact to an output device, and an ablation power generator configured to provide at least one electrical signal to the electrodes in order to ablate the tissue of the cavity.

Further in accordance with an embodiment of the present invention the processor is configured to assess the quality of contact of the electrodes with the tissue responsively to a first velocity measurement of the blood flow in the cavity prior to inflation of the inflatable balloon and a second velocity measurement of the blood flow in the cavity after inflation of the inflatable balloon.

Still further in accordance with an embodiment of the present invention the processor is configured to assess the quality of contact of the electrodes with the tissue responsively to a ratio of the first velocity measurement to the second velocity measurement.

Additionally, in accordance with an embodiment of the present invention the processor is configured to select the first velocity measurement for use in assessing the quality of contact responsively to receiving a user input confirming that the ultrasound probe is correctly placed to provide the velocity measurements of the blood flow in the cavity.

Moreover, in accordance with an embodiment of the present invention, the system includes a display, wherein the processor is configured to render to the display an instruction to position the ultrasound probe in the cavity, an instruction to confirm that the ultrasound probe is correctly placed to provide the velocity measurements of the blood flow in the cavity, and an instruction to inflate the inflatable balloon.

Further in accordance with an embodiment of the present invention the processor is configured to output the indication of the quality of contact responsively to the quality of contact exceeding a threshold quality of contact.

Still further in accordance with an embodiment of the present invention the velocity measurements of blood flow are peak velocity measurements of blood flow in the cavity over time.

Additionally, in accordance with an embodiment of the present invention, the system includes a display, wherein the ultrasound probe is configured to capture a plurality of two-dimensional (2D) ultrasonic images, and the processor configured is configured to render the 2D ultrasonic images to the display.

There is also provided in accordance with another embodiment of the present invention, a medical method, including inserting a catheter into a cavity of a body of a living subject, pressing electrodes of an inflatable balloon of the catheter against tissue of the cavity and at least partially blocking blood flow in the cavity, providing velocity measurements of blood flow in the cavity over time, assessing a quality of contact of the electrodes with tissue of the cavity responsively to at least one of the velocity measurements of the blood flow in the cavity, outputting an indication of the quality of contact to an output device, and providing at least one electrical signal to the electrodes in order to ablate the tissue of the cavity.

Moreover, in accordance with an embodiment of the present invention the assessing includes assessing the quality of contact of the electrodes with the tissue responsively to a first velocity measurement of the blood flow in the cavity prior to inflation of the inflatable balloon and a second velocity measurement of the blood flow in the cavity after inflation of the inflatable balloon.

Further in accordance with an embodiment of the present invention the assessing includes assessing the quality of contact of the electrodes with the tissue responsively to a ratio of the first velocity measurement to the second velocity measurement.

Still further in accordance with an embodiment of the present invention, the method includes selecting the first velocity measurement for use in assessing the quality of contact responsively to receiving a user input confirming that an ultrasound probe is correctly placed to provide the velocity measurements of the blood flow in the cavity.

Additionally, in accordance with an embodiment of the present invention, the method includes rendering to a display an instruction to position the ultrasound probe in the cavity, an instruction to confirm that the ultrasound probe is correctly placed to provide the velocity measurements of the blood flow in the cavity, and an instruction to inflate the inflatable balloon.

Moreover, in accordance with an embodiment of the present invention the outputting includes outputting the indication of the quality of contact responsively to the quality of contact exceeding a threshold quality of contact.

Further in accordance with an embodiment of the present invention the velocity measurements of blood flow are peak velocity measurements of blood flow in the cavity over time.

Still further in accordance with an embodiment of the present invention, the method includes capturing a plurality of two-dimensional (2D) ultrasonic images, and rendering the 2D ultrasonic images to a display.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
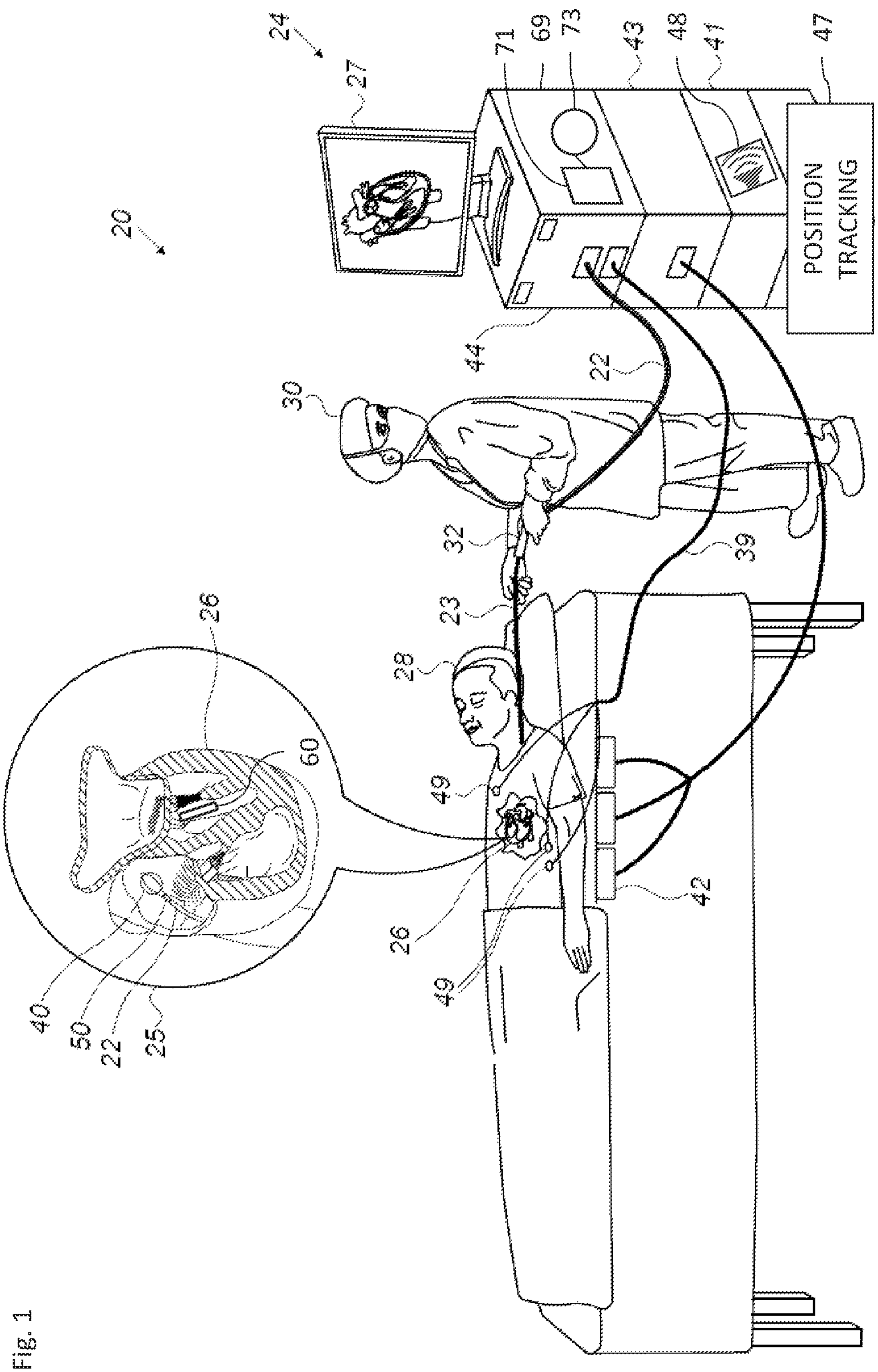
FIG. 1 is a schematic pictorial illustration of a medical system in accordance with an exemplary embodiment of the present invention.

Optimal alignment and contact of all active catheter electrodes (e.g., electrodes of a balloon catheter with the pulmonary vein (PV) antrum or any other body part) provides a greater probability of a successful single-shot ablation. Therefore, it is important to determine that the balloon catheter electrodes are correctly positioned against the tissue (e.g., of the PV and there is good contact/closure with the PV ostia before starting ablation).

One solution is to inject contrast and use fluoroscopy to see if the balloon prevents flow of the contrast past the body part, e.g., PV. Another solution is to examine a color doppler measured by an ultrasound probe to see if the balloon prevents blood flow past the body part, e.g., PV. However, it is very difficult for a physician to accurately estimate the quality of contact from the contrast or the color doppler. For example, with the color doppler, the balloon casts a shadow in the ultrasound image making the color, which represents the blood flow, difficult to be assessed by the physician.

Therefore, embodiments of the present invention solve the above problems by assessing a quality of contact of the electrodes of an inflatable balloon with tissue of a cavity (e.g., PV) responsively to one or more velocity measurements of blood flow in a cavity (e.g., PV). The measurements of blood flow are supplied by an ultrasound probe, which performs the measurements based on the doppler functionality of the probe.

In some cases, any one of the electrodes may be in contact with the tissue with full or partial contact or via another fluid such as blood of various thicknesses. The term "quality of contact" as used in the specification and claims is defined herein as an indicator of the degree of electrical contact between the catheter electrodes as a whole and the tissue. The "quality of contact" is expressed indirectly in terms of, or based on, blood flow velocity in the cavity in which the catheter is inserted.

In some embodiments, the quality of contact is assessed based on comparing the current velocity of blood flow in the cavity with a previous reference velocity of blood flow in the cavity, for example, from a time when the balloon was not inflated or not positioned to block blood flow in the cavity. The quality of contact may be based on a ratio of the current velocity of blood flow in the cavity to the reference velocity of blood flow in the cavity, so as the current velocity of blood flow in the cavity decreases, the ratio decreases, thereby indicating a better quality of contact of the electrodes with the tissue of the cavity.

In some embodiments, the quality of contact may be computed based on a reduction in the velocity of the blood flow from the reference velocity. The quality of contact may be expressed as a percentage (or fractional) reduction in blood flow velocity or as an absolute reduction in blood flow velocity.

The blood flow velocity used in the above computations may be the peak blood flow velocity in the cavity or any other suitable measure (e.g., average blood flow velocity).

In some embodiments, the current quality of contact may be rendered to a display (and/or output to another output device, e.g., as an audio output) and the value is updated as the current quality of contact changes. The quality of contact may be expressed as a percentage, a fraction, a value between 0 and 1, and/or as a textual indication such as "poor", "fair", "good", and "excellent" depending on the level of quality of contact, or "insufficient contact" or "sufficient contact".

In some embodiments, the quality of contact is only rendered to the display and/or output device when the level of the quality of contact exceeds a given threshold.

In response to the quality of contact exceeding a given threshold, the physician may perform the ablation. In some embodiments, ablation may be automatically stopped, or a warning provided, if the quality of contact no longer exceeds the given threshold.

System Description

Figure 2:
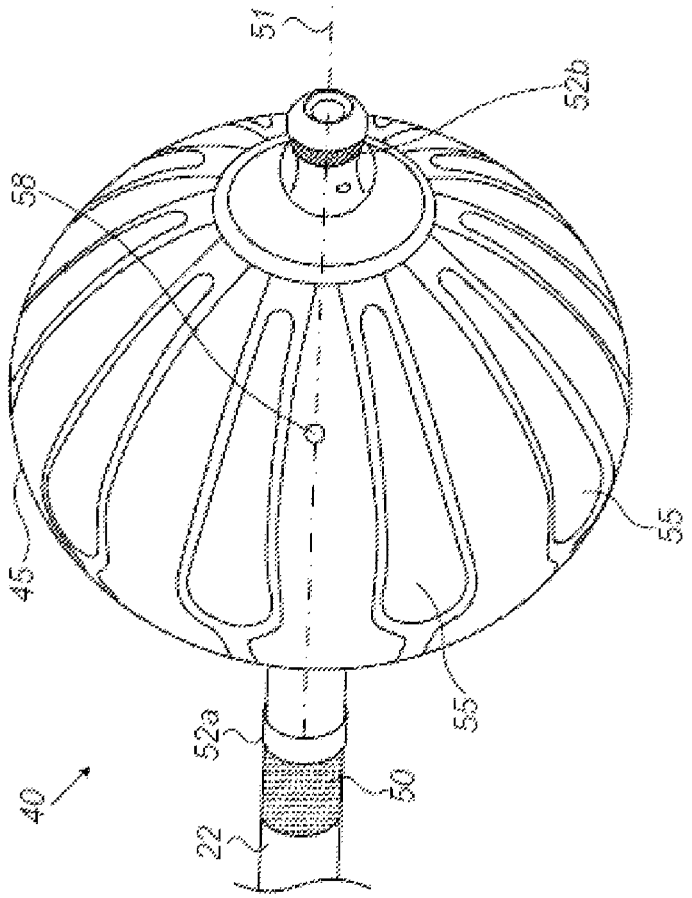
FIG. 2 is a schematic pictorial illustration of a balloon catheter used in the system of FIG. 1.

Reference is now made to FIG. 1, which is a schematic pictorial illustration of a medical system 20 in accordance with an embodiment of the present invention. Reference is also made to FIG. 2, which is a schematic pictorial illustration of a balloon catheter 40, in accordance with an embodiment of the present invention.

The medical system 20 is used to determine the position of the balloon catheter 40, seen in an inset 25 of FIG. 1 and in more detail in FIG. 2. The balloon catheter 40 includes a shaft 22 and an inflatable balloon 45 fitted at a distal end of the shaft 22. The catheter 40 is configured to be inserted into a body part of a living subject. Typically, the balloon catheter 40 is used for therapeutic treatment, such as spatially ablating cardiac tissue, for example at the left atrium.

The medical system 20 can determine a position and orientation of the shaft 22 of the balloon catheter 40 based on sensing-electrodes 52 (proximal-electrode 52*a* disposed on the shaft 22 and distal-electrode 52*b* disposed at the distal end of the inflatable balloon 45) and a magnetic sensor 50 fitted just proximally to proximal-electrode 52*a*. The proximal-electrode 52*a*, the distal-electrode 52*b*, and the magnetic sensor 50 are connected by wires running through the shaft 22 to various driver circuitries in a console 24. In some embodiments, the distal electrode 52*b* may be omitted.

The shaft 22 defines a longitudinal axis 51. A center point 58 on the axis 51, which is the origin of the sphere shape of the inflatable balloon 45, defines a nominal position of the inflatable balloon 45. The catheter 40 includes multiple catheter electrodes 55 disposed on the inflatable balloon 45 or on any suitable expandable distal end assembly, around the longitudinal axis 51. In some embodiments, the catheter electrodes 55 are disposed in a circumference over the inflatable balloon 45, which occupy a large area as compared with sensing-electrodes 52*a* and 52*b*. The catheter electrodes 55 are configured to contact tissue at respective locations within the body part. Radio frequency (RF) power or other suitable signals may be supplied to the catheter electrodes 55 to ablate the tissue, e.g., cardiac tissue using RF ablation or irreversible electroporation (IRE).

Typically, the disposed catheter electrodes 55 are evenly distributed along an equator of the inflatable balloon 45, where the equator is generally aligned perpendicular to the longitudinal axis 51 of the distal end of the shaft 22.

The illustration shown in FIG. 2 is chosen purely for the sake of conceptual clarity. Other configurations of sensing-electrodes 52 and catheter electrodes 55 are possible. Additional functionalities may be included in the magnetic sensor 50. Elements which are not relevant to the disclosed embodiments of the invention, such as irrigation ports, are omitted for the sake of clarity.

A physician 30 navigates the balloon catheter 40 to a target location in a heart 26 of a patient 28 by manipulating the shaft 22 using a manipulator 32 near the proximal end of the catheter and/or deflection from a sheath 23. The balloon catheter 40 is inserted, while the inflatable balloon 45 is deflated, through the sheath 23, and only after the balloon catheter 40 is retracted from the sheath 23 is the inflatable balloon 45 inflated and regains its intended functional shape. By containing balloon catheter 40 in a deflated configuration, the sheath 23 also serves to minimize vascular trauma on its way to the target location.

Console 24 comprises processor 41, typically a general-purpose computer and a suitable front end and interface circuits 44 for generating signals in, and/or receiving signals from, body surface electrodes 49 which are attached by wires running through a cable 39 to the chest and to the back of the patient 28.

The system 20 includes a position tracking sub-system 47, which may comprise a magnetic-sensing sub-system at least partially disposed in the console 24. The patient 28 is placed in a magnetic field generated by a pad containing magnetic field generator coils 42, which are driven by a unit 43 disposed in the console 24. The magnetic fields generated by the coils 42 generate directional signals in the magnetic sensor 50, which are then provided as corresponding electrical inputs to the processor 41.

In some embodiments, the processor 41 uses the position-signals received from the sensing-electrodes 52 (and/or the body surface electrodes 49), the magnetic sensor 50, and the catheter electrodes 55 to estimate a position of the balloon catheter 40 inside an organ, such as inside a cardiac chamber. In some embodiments, the processor 41 correlates the position signals received from the electrodes 52, 55 with previously acquired magnetic location-calibrated position signals, to estimate the position of the balloon catheter 40 inside a cardiac chamber. The position coordinates of the sensing-electrodes 52 and the catheter electrodes 55 may be determined by the processor 41 based on, among other inputs, measured impedances, or on proportions of currents distribution, between the electrodes 52, 55 and the surface electrodes 49. The console 24 drives a display 27, which shows the distal end of the catheter position inside the heart 26.

The method of position sensing using current distribution measurements and/or external magnetic fields is implemented in various medical applications, for example, in the Carto® system, produced by Biosense Webster Inc. (Irvine, California), and is described in detail in U.S. Pat. Nos. 5,391,199, 6,690,963, 6,484,118, 6,239,724, 6,618,612, 6,332,089, 7,756,576, 7,869,865, and 7,848,787, in PCT Patent Publication WO 96/05768, and in U.S. Patent Application Publication Nos. 2002/0065455 A1, 2003/0120150 A1 and 2004/0068178 A1.

The Carto®3 system applies an Active Current Location (ACL) impedance-based position-tracking method. In some embodiments, using the above noted ACL method, the processor 41 estimates the positions of the sensing-electrodes 52 and the catheter electrodes 55. In some embodiments, the signals received from the electrodes 52, 55 are correlated with a matrix which maps impedance (or another electrical value) measured by the sensing-electrodes 52, 55 with a position that was previously acquired from magnetic location-calibrated position signals.

In some embodiments, to visualize catheters which do not include a magnetic sensor, the processor 41 may apply an electrical signal-based method, referred to as the Independent Current Location (ICL) method. In the ICL method, the processor 41 calculates a local scaling factor for each voxel of a volume of the balloon catheter 40. The factor is determined using a catheter with multiple electrodes having a known spatial relationship, such as a Lasso-shaped catheter.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The system 20 may also include a sound outputting device 48 configured to provide an audio output, described in more detail with reference to FIG. 4.

The system 20 also includes an ablation power generator 69 (such as an RF signal generator) configured to provide at least one electrical signal to the electrodes 55 in order to ablate the tissue of the body part or cavity. For example, the ablation power generator 69 may be connected to the catheter 40, and apply electrical signals between adjacent catheter electrodes 55. The medical system 20 may also include an irrigation reservoir 71 configured to store irrigation fluid, and a pump 73 configured to be connected to the irrigation reservoir 71 and the catheter 40, and to pump the irrigation fluid from the irrigation reservoir 71 via an irrigation tube (not shown) through irrigation holes (not shown) of the catheter 40.

FIG. 1 shows only elements related to the disclosed techniques, for the sake of simplicity and clarity. The system 20 typically comprises additional modules and elements that are not directly related to the disclosed techniques, and thus are intentionally omitted from FIG. 1 and from the corresponding description.

Figure 3:
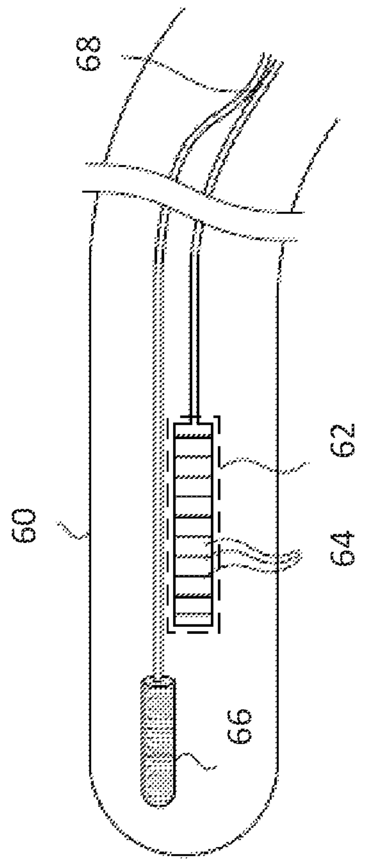
FIG. 3 is a schematic side view of the distal end of an ultrasound catheter used in the system of FIG. 1.

Reference is now made to FIG. 3, which is a schematic side view of the distal end of an ultrasound catheter 60 used in the system 20 of FIG. 1. Reference is also made to FIG. 1.

The system 20 and catheter 60 are shown here by way of illustration, to assist in understanding the methods of ultrasound-based imaging that are described further below. These methods, however, are not limited to catheter-based ultrasonic sensing and may similarly be applied, mutatis mutandis, using 2D or 3D ultrasound images acquired by other types of probes, both intra- and extra-corporeal. Furthermore, these methods may be used in imaging of other anatomical cavities, not only in the heart 26.

A variety of devices and methods for intracardiac ultrasonic imaging are known in the art. For example, Biosense Webster Inc. (Irvine, California) offers the CartoSound™ system and SoundStar™ catheter for producing 3D ultrasound images in real time. The SoundStar catheter, which is inserted through the vascular system into the heart, contains a position sensor and a phased array of ultrasound transducers. The CartoSound system processes the signals from the position sensor and the ultrasound transducers to generate 3D images of the heart chambers.

As shown in FIG. 1, the physician 30, inserts catheter 60 into the body of a patient 28, so that the distal end of the catheter 60 passes through the vascular system into the patient's heart 26. The catheter is connected at its proximal end to the console 24. The processor 41 receives and processes signals from catheter 60, as described hereinbelow. Typically, console 24 also enables a user to observe and regulate the functions of catheter 60 and to view and edit images that are formed using the catheter 60. For these purposes, the console comprises the display 27 and a user interface (not shown).

As shown in FIG. 3, the distal end of catheter 60 comprises an ultrasound imaging device (or probe) 62, which is used to produce ultrasound images of the inside of the body. Device 62 typically comprises a phased array of transducers 64, which is operated, as is known in the art, so as to capture a two-dimensional (2D) "fan" image in the plane of the scanning ultrasonic beam (referred to herein as the "beam plane" or "image plane"), which contains the longitudinal axis of the catheter 60. The transducers 64 receive ultrasonic waves that are reflected from objects in the beam plane and output signals in response to the reflected waves. Typically, these signals are conveyed by wires 68 running through catheter 60 to console 24, which processes the signals in order to form and display ultrasound images and optionally 3D maps, as described hereinbelow.

The distal end of catheter 60 further comprises a position sensor 66, which generates signals that indicate the position (location and orientation including roll) of the catheter 60 within the body. Based on these position signals, console 24 may determine the location and orientation of each fan image captured by imaging device 62. Processor 41 is thus able to determine the coordinates of objects appearing in the fan image, as well as to register and combine multiple 2D images captured at different catheter positions.

In the pictured embodiment, system 20 uses magnetic position sensing to determine position coordinates of the distal end of catheter 60 inside heart 26 as described above with reference to FIG. 1. Sensor 66, which may comprise, for example, a magnetic position sensor including one or more coils within the distal end of catheter 60, generates electrical signals in response to the magnetic fields of the magnetic field generator coils 42. Processor 41 processes these signals in order to determine the position (location and orientation) coordinates of the distal end of catheter 60. Console 24 may use the coordinates in driving display 27 to show the location and status of the catheter.

This method of position sensing and processing is implemented in the CARTO® 3 system produced by Biosense Webster Inc. This sort of magnetic position sensing is described in detail, for example, in U.S. Pat. No. 6,266,551. Other systems that combine ultrasonic imaging with magnetic position sensing are described in U.S. Pat. Nos. 6,690,963, 6,716,166 and 6,773,402.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter

60 that causes console 24 to receive signals indicative of the coordinates of the element. The position transducer may thus comprise a receiver in the catheter, such as sensor 66, which generates a position signal to the console 24 based on energy received by the transducer; or it may comprise a transmitter, emitting energy that is sensed by a receiver external to the probe 60. Furthermore, the methods described hereinbelow may similarly be applied in mapping and imaging applications using not only catheters, but also probes of other types, both in the heart and in other body organs and regions, as well as ultrasound probes external to the body.

The 2D ultrasonic images may be processed by the processor 41 to generate an anatomical map of one or more chambers of the heart 26 using any suitable method, for example the method described in US Patent Publication No. 2011/0152684. In some embodiments, an anatomical map of one or more chambers of the heart 26 may be generated based on signals provided by an electrode catheter (such as the balloon catheter 40, or a basket catheter or a multi-spline catheter) inserted into chambers of the heart using any suitable method, for example the method described in U.S. Pat. No. 10,918,310.

Figure 4:
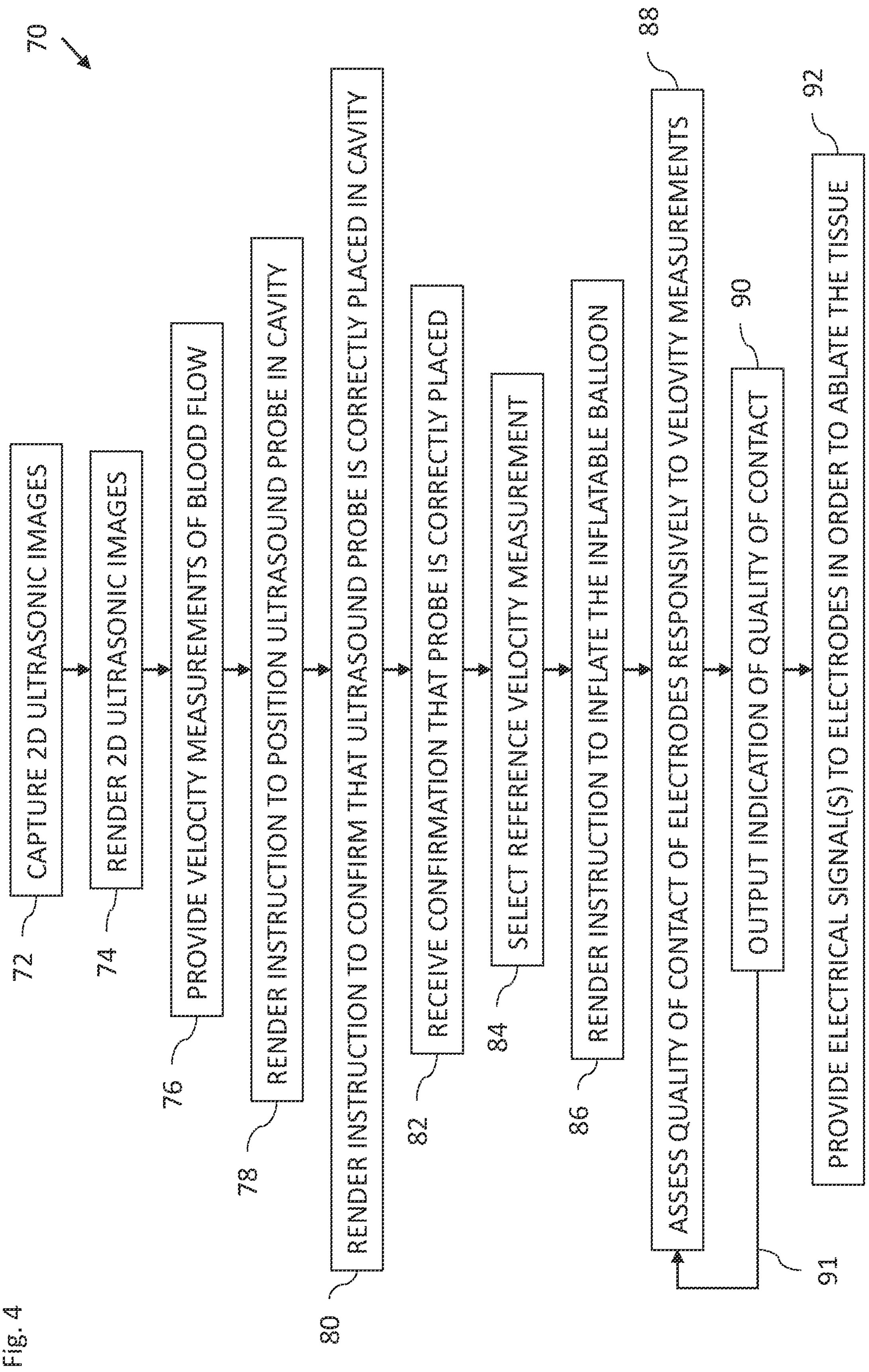
FIG. 4 is a flowchart including steps in a method of operation of the system of FIG. 1.

Reference is now made to FIG. 4, which is a flowchart 70 including steps in a method of operation of the system 20 of FIG. 1. Reference is also made to FIG. 1.

The balloon catheter 40 is configured to be inserted into a cavity (e.g., a chamber of the heart 26) of a body of a living subject (e.g., the patient 28). The inflatable balloon 45 may be guided to cavity by the physician 30 with the aid of an anatomical map rendered to the display 27 with a representation of the balloon catheter 40 superimposed thereon based on position tracking of the balloon catheter 40 as described above in more detail with reference to FIGS. 1 and 2. In some embodiments, the balloon catheter 40 may be guided using any suitable method, for example, based on imaging the balloon catheter 40 in the body using fluoroscopy or ultrasound imaging.

Figure 5:
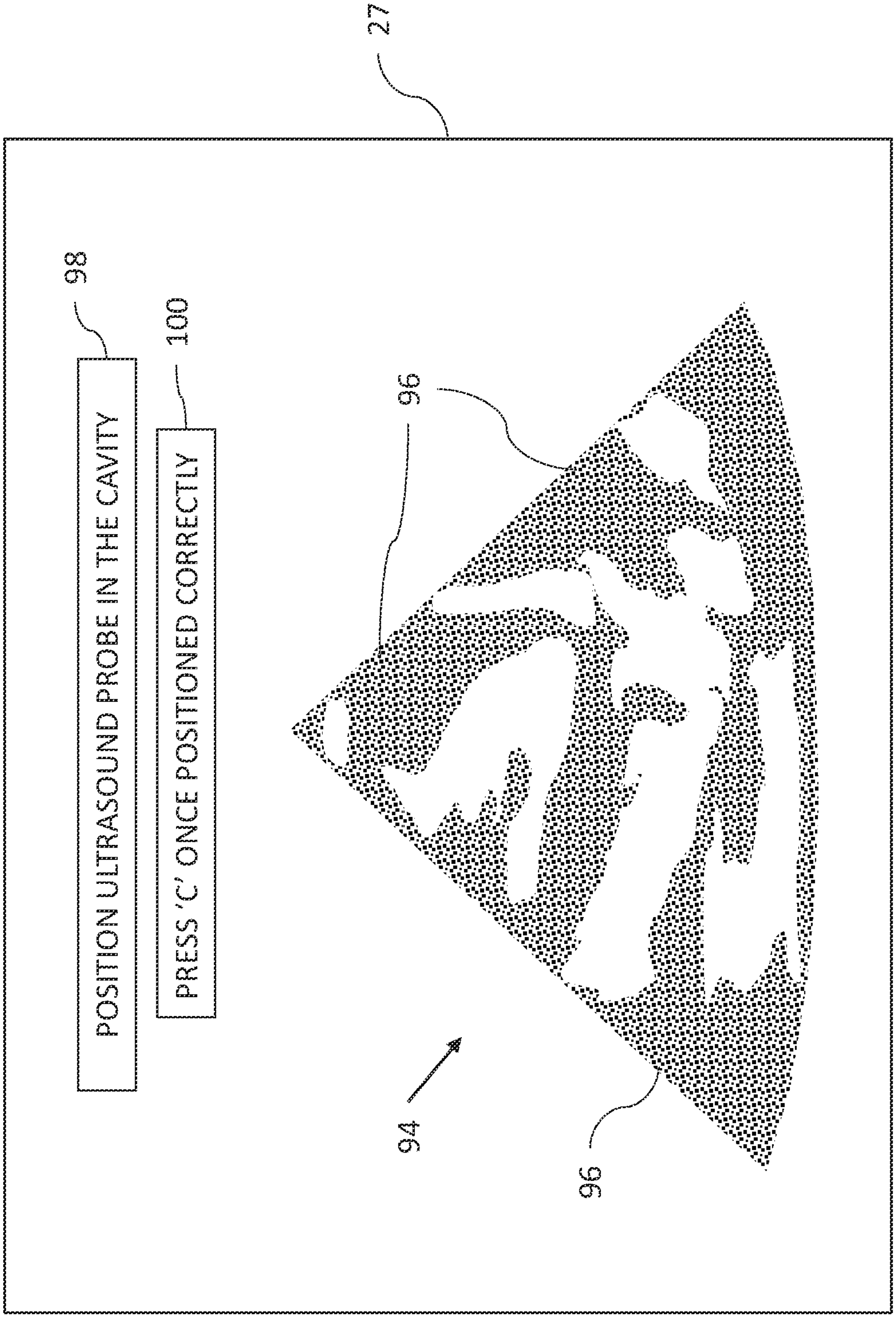
FIGS. 5-8 are schematic views of screenshots to illustrate the method of FIG. 4.

Reference is now made to FIGS. 4 and 5.

The ultrasound catheter 60 (FIG. 3) is inserted into the cavity (e.g., a chamber of the heart 26) of the body. The ultrasound catheter 60 is typically inserted into a different chamber of the heart 26 from which the balloon catheter 40 is inserted. The ultrasound imaging device 62 is configured to capture (block 72) two-dimensional (2D) ultrasonic images 94 (only one shown in FIG. 5). The processor 41 is configured to render (block 74) the 2D ultrasonic images 94 to the display 27. The image has the form of a 2D fan, with its vertex at imaging device 62. As noted above, console 24 can determine the location of the vertex and the orientation of the fan in 3D space based on the signals received from position sensor 66. Dark areas 96 in the image 94 correspond to areas, such as the heart chambers, that are filled with blood and therefore have low reflectance. Brighter areas generally represent tissue, such as the internal and external heart walls.

The ultrasound imaging device 62 is configured to provide (block 76) velocity measurements of the blood flow in the cavity over time using doppler functionality of the ultrasound imaging device 62. In some embodiments, the velocity measurements of blood flow are peak velocity measurements of blood flow in the cavity over time. The ultrasound imaging device 62 may provide two measurements of velocity (e.g., peak or mean velocity) in the cavity, for example, the velocity of blood flowing away from the ultrasound imaging device 62 and the velocity of blood flowing towards the ultrasound imaging device 62. In some embodiments, the physician 30 may select whether the velocity of blood flowing away from the ultrasound imaging device 62 or the velocity of blood flowing towards the ultrasound imaging device 62 should be used in assessing the quality of contact described below in more detail with reference to the step of block 88.

The processor 41 is configured to render (block 78) to the display 27 an instruction 98 to position the ultrasound imaging device 62 in the cavity. The processor 41 is configured to render (block 80) to the display 27 an instruction 100 to confirm that the ultrasound imaging device 62 is correctly placed to provide the velocity measurements of the blood flow in the cavity. The physician 30 may position the ultrasound imaging device 62 correctly in the cavity based on observing the ultrasonic images 94 or a representation of the ultrasound catheter 60 superimposed on an anatomic map or by using any suitable imaging method.

Figure 6:
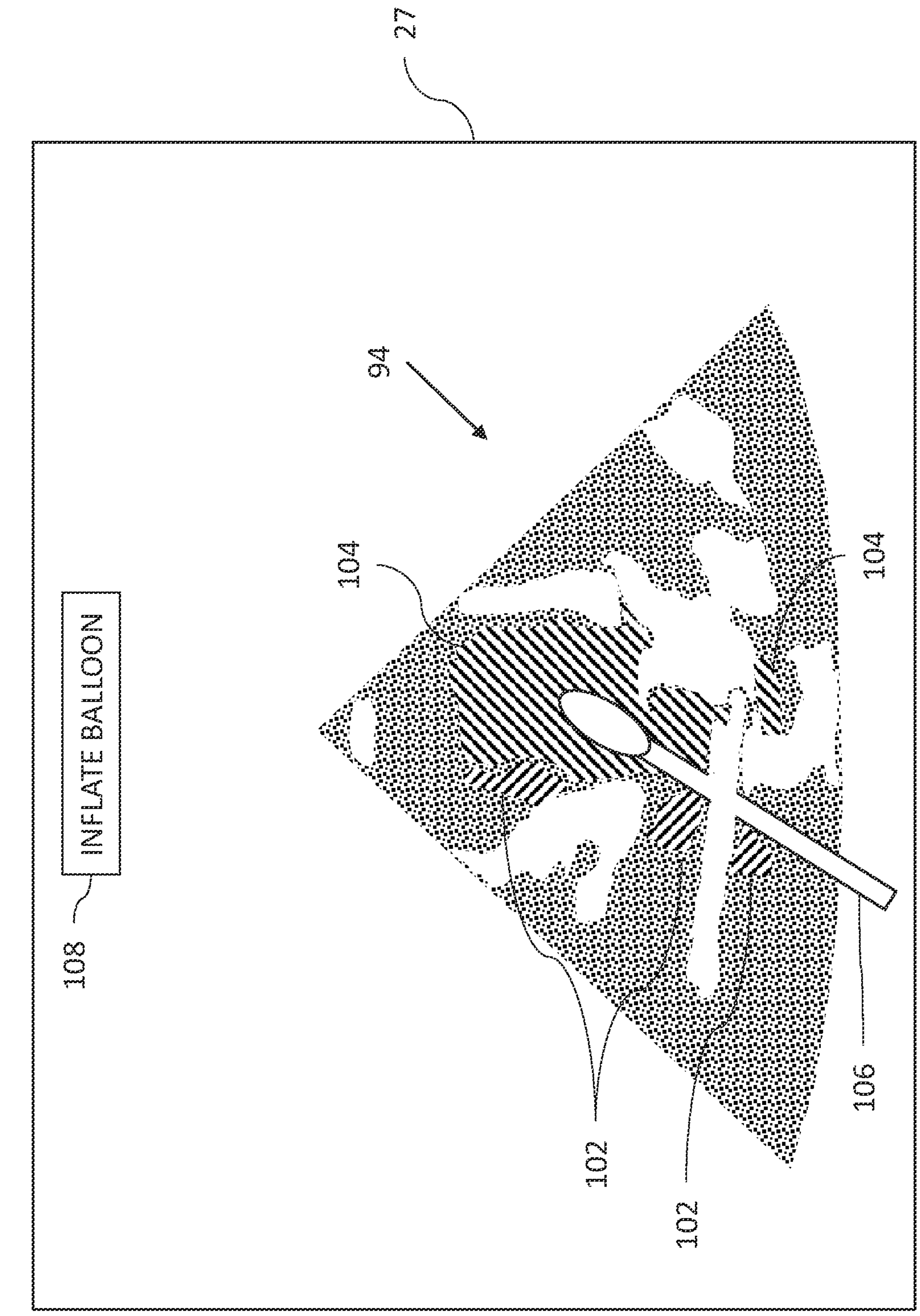

Reference is now made to FIGS. 4 and 6. The ultrasonic image 94 shown in FIG. 6 is an image of the cavity with the ultrasound imaging device 62 correctly placed to provide the velocity measurements of the blood flow in the cavity. The ultrasonic images 94 also includes blood flow indicators to show the blood flow detected by the ultrasound imaging device 62. FIG. 6 shows blood flowing away (shaded regions 102) from the ultrasound imaging device 62 and blood flowing towards (shaded regions 104) the ultrasound imaging device 62. Rendering the shaded regions 102, and the shaded regions 104 on the ultrasonic images 94 is optional and does not affect the provision of the velocity measurements of the blood flow in the cavity by the ultrasound imaging device 62. However, the shaded regions 102 and shaded regions 104 may aid the physician 30 in correctly positioning the ultrasound imaging device 62 in the cavity.

Although not part of the ultrasonic images 94, a representation 106 of the balloon catheter 40 is also shown in FIG. 6 for the sake of better understanding the method of operation of the system 20. In some embodiments, the representation 106 of the balloon catheter 40 may be superimposed over the ultrasonic image 94. In other embodiments, the representation 106 of the balloon catheter 40 is not shown superimposed over the ultrasonic image 94. The balloon catheter 40 is shown with the inflatable balloon 45 in its non-inflated state.

The processor 41 is configured to receive (block 82) a user input confirming that the ultrasound imaging device 62 is correctly placed to provide the velocity measurements of the blood flow in the cavity.

The processor 41 is configured to select (block 84) a velocity measurement (hereinafter referred to as the "reference velocity measurement") for use in assessing the quality of contact, responsively to receiving the user input confirming that the ultrasound imaging device 62 is correctly placed to provide the velocity measurements of the blood flow in the cavity. The reference velocity measurement is selected from one of the velocity measurements provided by the ultrasound imaging device 62 after the ultrasound imaging device 62 is correctly placed in the cavity to provide velocity measurements of blood flow in the cavity, and prior to the inflatable balloon 45 being inflated, or prior to the inflatable balloon 45 blocking blood flow in the cavity. The processor 41 is configured to render (block 86) to the display 27 an instruction 108 to inflate the inflatable balloon 45.

Figure 7:
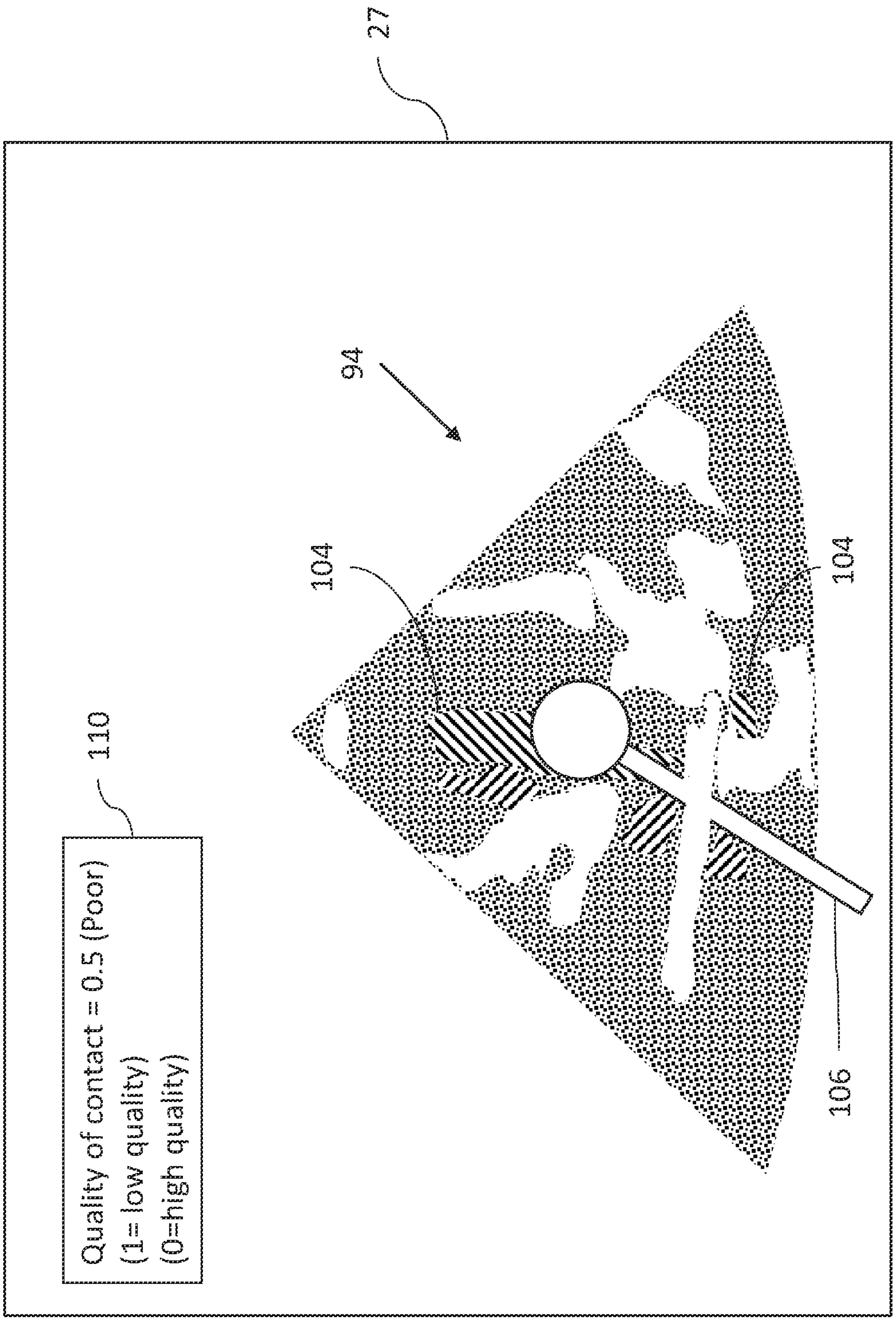
Figure 8:
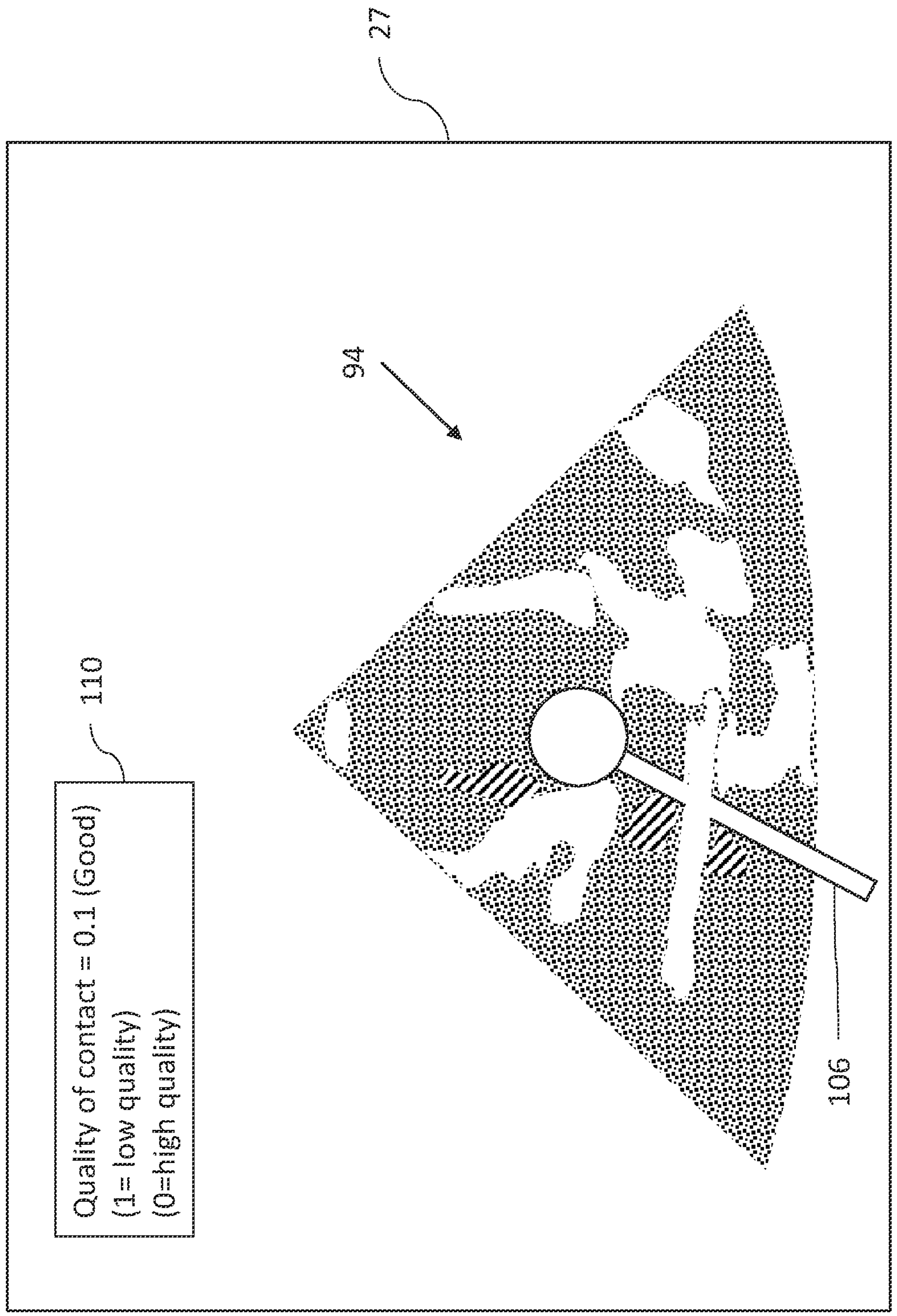

Reference is now made to FIGS. 4, 7, and 8.

The physician 30 inflates the inflatable balloon 45 using a control on the manipulator 32 or console 24. The inflatable balloon 45 is configured to press the electrodes 55 (FIG. 2) of the inflatable balloon 45 against tissue of the cavity and at least partially block blood flow in the cavity. FIG. 7 shows the representation 106 of the inflatable balloon 45 in an inflated state partially blocking blood flow in the cavity. The shaded regions 104 of the ultrasonic image 94 in FIG. 7 representing the blood flow towards the ultrasound imaging device 62 are smaller than in FIG. 6. FIG. 7 also shows an example indication 110 for the quality of contact of the catheter electrodes 55 with the tissue as equal to "0.5" or "poor". FIG. 8 shows the representation 106 of the inflatable balloon 45 in a different position than shown in FIG. 7. In FIG. 8, the representation 106 of the inflatable balloon 45 is seen providing better blockage of blood flow in the cavity (evidenced by the absence of the shaded regions 104) and therefore providing better contact between the catheter electrodes 55 of the inflatable balloon 45 and the tissue of the cavity. FIG. 8 also shows an example indication 110 for the quality of contact of the catheter electrodes 55 with the tissue as equal to "0.1" or "good".

The processor 41 is configured to assess (block 88) a quality of contact of the electrodes 55 (FIG. 2) with the tissue of the cavity responsively to at least one of the velocity measurements of the blood flow in the cavity. In some embodiments, the processor 41 is configured to assess the quality of contact of the electrodes with the tissue responsively to the reference velocity measurement ($V_R$) of the blood flow in the cavity (e.g., prior to inflation of the inflatable balloon 45) and a current velocity measurement ($V_C$) of the blood flow in the cavity after inflation of the inflatable balloon 45.

In some embodiments, the processor 41 is configured to assess the quality of contact of the electrodes 55 with the tissue responsively to a ratio of the reference velocity measurement to the current velocity measurement. For example, the ratio may be expressed as $V_R$:$V_C$, or $V_C$:$V_R$, or $V_C/V_R$, or $V_R/V_C$. The quality of contact may be expressed as a fraction, or as a value between 0 and 1, or as a percentage (e.g., $V_C/V_R \times 100$).

In some embodiments, the processor 41 is configured to assess the quality of contact of the catheter electrodes 55 with the tissue as a reduction in the velocity of the blood flow. For example, the quality of contract may be expressed as an absolute reduction, e.g., $V_R$ less $V_C$, or as a fractional or percentage reduction, e.g., $(V_R-V_C)/V_R$, $(V_R-V_C)/V_R \times 100$.

In some embodiments, the quality of contact may be expressed as a qualitive indication such as "poor", "fair", "good", and "excellent", or "insufficient contact" or "sufficient contact" according to the values of $V_R$ and $V_C$. For example, if $V_C/V_R$ is 0.5 or greater, then the quality of contact is "poor", if $V_C/V_R$ is between 0.3 and 0.5, then the quality of contact is "fair", if $V_C/V_R$ is between 0.1 and 0.3, then the quality of contact is "good", and if $V_C/V_R$ is less than 0.1 then the quality of contact is "excellent".

The processor 41 is configured to output (block 90) the indication 110 of the quality of contact to an output device (such as to the sound outputting device 48 as an audio indication and/or to the display 27 as a visual indication).

The steps of blocks 88 and 90 are repeated (arrow 91). As the value of $V_C$ changes, the quality of contact changes, and the processor 41 is configured to output the indication 110 of the updated quality of contact to the output device.

In some embodiments, the processor 41 is configured to output the indication 110 to the output device after the step of block 84. In some embodiments, the processor 41 is configured to output the indication 110 of the quality of contact responsively to the quality of contact exceeding a threshold quality of contact (whereas prior to the quality of contact exceeding the threshold, the indication 110 is not output to the output device).

Once the catheter electrodes 55 are in sufficient contact with the tissue of the cavity as indicated by the quality of contact, the physician 30 may then activate the ablation power generator 69 to provide (block 92) signal(s) to the catheter electrodes 55 in order to ablate tissue of the cavity. In some embodiments, the processor 41 may be configured to automatically stop the ablation power generator 69 providing the signal(s) to the electrodes 55, or provide a warning responsively to the quality of contact no longer exceeding the threshold quality of contact.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:

a catheter configured to be inserted into a chamber of a heart of a living subject, the catheter having a longitudinal axis and an inflatable balloon comprising electrodes, the inflatable balloon being configured to press the electrodes against tissue of the chamber and at least partially block blood flow in the chamber;

an ultrasound probe configured to be inserted, separately from and independent of the catheter, into the chamber of the heart in which the catheter is inserted or a different chamber of the heart to provide a plurality of velocity measurements of the blood flow in the chamber over time, the ultrasound probe being further configured to capture an image in an image plane that contains the longitudinal axis of the catheter;

a processor configurable to:

obtain from the ultrasound probe a first velocity measurement from the plurality of velocity measurements prior to inflation of the inflatable balloon and a second velocity measurement of the blood flow in the chamber after inflation of the inflatable balloon and determine a quality of contact of the electrodes with the tissue in the chamber in response to one of: i) a ratio of the first velocity measurement to the second velocity measurement, ii) an absolute reduction or fractional percentage reduction in the first velocity measurement with respect to the second velocity measurement, or iii) a ratio of the second velocity measurement to the first velocity measurement;

select the first velocity measurement for use in determining the quality of contact responsively to receiving a user input confirming that the ultrasound probe is correctly placed to provide the velocity measurements of the blood flow in the chamber; and output an indication of the quality of contact to an output device; and an ablation power generator configured to provide at least one electrical signal to the electrodes in order to ablate the tissue of the chamber.

2. The system according to claim 1, wherein the processor is configurable to render on a display:

an instruction to position the ultrasound probe in the chamber;

an instruction to confirm that the ultrasound probe is correctly placed to provide the velocity measurements of the blood flow in the chamber; and an instruction to inflate the inflatable balloon.

3. The system according to claim 1, wherein the processor is configurable to output the indication of the quality of contact responsively to the quality of contact exceeding a threshold quality of contact.

4. The system according to claim 1, wherein the velocity measurements of blood flow are peak velocity measurements of blood flow in the chamber over time.

5. The system according to claim 1, wherein the processor is configurable to render two-dimensional (2D) images captured by the ultrasound probe to a display.

6. A medical method, comprising:

inserting a catheter into a chamber of a heart of a living subject, the catheter having a longitudinal axis and an inflatable balloon comprising electrodes, the inflatable balloon being configured to press the electrodes against tissue of the chamber and at least partially block blood flow in the chamber;

inserting an ultrasound probe, separately from and independent of the catheter, into the chamber of the heart in which the catheter is inserted or a different chamber of the heart, the ultrasound probe being configured to provide a plurality of velocity measurements of the blood flow in the chamber over time and further configured to capture an image in an image plane that contains the longitudinal axis of the catheter; inflating the balloon of the catheter to press the electrodes against tissue of the chamber and at least partially blocking blood flow in the chamber;

obtaining from the ultrasound probe a first velocity measurement from the plurality of velocity measurements prior to inflation of the inflatable balloon and a second velocity measurement of the blood flow in the chamber after inflation of the inflatable balloon;

determining a quality of contact of the electrodes with tissue of the chamber, wherein the determining comprises selecting the first velocity measurement for use in determining the quality of contact responsively to receiving a user input confirming that the ultrasound probe is correctly placed to provide the velocity measurements of the blood flow in the chamber, the quality of contact being determined in response to one of: i) a ratio of the first velocity measurement to the second velocity measurement, ii) an absolute reduction or fractional percentage reduction in the first velocity measurement with respect to the second velocity measurement, or iii) a ratio of the second velocity measurement to the first velocity measurement;

outputting an indication of the quality of contact to an output device; and providing at least one electrical signal to the electrodes in order to ablate the tissue of the chamber.

7. The method according to claim 6, further comprising rendering to a display:

an instruction to position the ultrasound probe in the chamber;

an instruction to confirm that the ultrasound probe is correctly placed to provide the velocity measurements of the blood flow in the chamber; and an instruction to inflate the inflatable balloon.

8. The method according to claim 6, wherein the outputting includes outputting the indication of the quality of contact responsively to the quality of contact exceeding a threshold quality of contact.

9. The method according to claim 6, wherein the velocity measurements of blood flow are peak velocity measurements of blood flow in the chamber over time.

10. The method according to claim 6, further comprising:

capturing a plurality of two-dimensional (2D) ultrasonic images; and rendering the 2D ultrasonic images to a display.

11. The system according to claim 1, wherein the indication of the quality of contact comprises a value between 0 and 1.

* * * * *